(12) United States Patent
Werpy et al.

(10) Patent No.: US 8,501,963 B2
(45) Date of Patent: Aug. 6, 2013

(54) PROCESS FOR PRODUCING CYCLIC COMPOUNDS

(75) Inventors: Todd A. Werpy, W. Richland, WA (US); John G. Frye, Jr., Richland, WA (US); James F. White, Richland, WA (US); Johnathan E. Holladay, Kennewick, WA (US); Alan H. Zacher, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 13 days.

(21) Appl. No.: 13/175,601

(22) Filed: Jul. 1, 2011

(65) Prior Publication Data

US 2011/0263874 A1    Oct. 27, 2011

Related U.S. Application Data

(62) Division of application No. 12/702,818, filed on Feb. 9, 2010, now Pat. No. 7,973,177, which is a division of application No. 11/688,022, filed on Mar. 19, 2007, now Pat. No. 7,674,916, which is a division of application No. 10/731,108, filed on Dec. 10, 2003, now Pat. No. 7,199,250.

(60) Provisional application No. 60/435,469, filed on Dec. 20, 2002.

(51) Int. Cl.
*C07D 207/267* (2006.01)

(52) U.S. Cl.
USPC .......................................... 548/552; 546/290

(58) Field of Classification Search
USPC .......................................... 548/552; 546/290
See application file for complete search history.

(56) References Cited

U.S. PATENT DOCUMENTS

| | | | |
|---|---|---|---|
| 2,187,745 A | 1/1940 | Lazier |
| 2,267,757 A | 12/1941 | Schuster et al. |
| 2,674,602 A | 4/1954 | Schuster |
| 3,080,377 A | 3/1963 | Liao |
| 3,092,638 A | 6/1963 | Liao et al. |
| 3,109,005 A | 10/1963 | Lidov |
| 3,198,808 A | 8/1965 | Walldorf et al. |
| 3,448,118 A | 6/1969 | Chichery et al. |
| 3,634,346 A | 1/1972 | McKeon et al. |
| 3,637,743 A | 1/1972 | Prince |
| 3,661,894 A | 5/1972 | Wehner et al. |
| 3,681,387 A | 8/1972 | Hollstein et al. |
| 3,745,164 A | 7/1973 | Adamek |
| 3,767,644 A | 10/1973 | Fukuoka et al. |
| 3,775,431 A | 11/1973 | Rodewald |
| 3,812,148 A | 5/1974 | Hollstein et al. |
| 3,884,936 A | 5/1975 | Hollstein |
| 3,966,763 A | 6/1976 | Greene |
| 4,012,418 A | 3/1977 | Schaafsma et al. |
| 4,151,171 A | 4/1979 | Kurkov |
| 4,152,331 A | 5/1979 | Meijer et al. |
| 4,263,175 A | 4/1981 | Pesa et al. |
| 4,356,124 A | 10/1982 | Pesa et al. |
| 4,404,391 A | 9/1983 | Meyer et al. |
| 4,420,620 A | 12/1983 | Murib |
| 4,731,454 A | 3/1988 | Otake et al. |
| 4,780,547 A | 10/1988 | zu Hauser et al. |
| 4,800,227 A | 1/1989 | Matson |
| 4,814,464 A | 3/1989 | Olsen |
| 4,841,069 A | 6/1989 | Olsen |
| 4,851,546 A | 7/1989 | Graham et al. |
| 4,885,371 A | 12/1989 | Tracy et al. |
| 4,904,804 A | 2/1990 | Matson |
| 5,101,044 A | 3/1992 | Schuster et al. |
| 5,101,045 A | 3/1992 | Koehler et al. |
| 5,106,730 A | 4/1992 | Van Ness et al. |
| 5,157,127 A | 10/1992 | Weyer et al. |
| 5,276,165 A | 1/1994 | Weyer et al. |
| 5,338,861 A | 8/1994 | Botta et al. |
| 5,347,021 A | 9/1994 | Taylor et al. |
| 5,401,856 A | 3/1995 | Grey et al. |

(Continued)

FOREIGN PATENT DOCUMENTS

| | | |
|---|---|---|
| CN | 1104635 | 7/1995 |
| CN | 1173492 | 2/1998 |
| CS | 146054 | 11/1972 |
| CS | 191496 | 7/1979 |
| CS | 212181 | 2/1982 |
| DE | 2025172 | 1/1971 |
| DE | 2165643 | 7/1972 |
| DE | 3701297 | 7/1988 |
| DE | 19626123 | 1/1998 |
| EP | 0027022 | 4/1981 |

(Continued)

OTHER PUBLICATIONS

Patton et al., University of Florida "Regenerable N-Alkylamide Hydroperoxide for Catalyiic Substrate Oxidation" 1993, pp. 1611-1615.
Nghiem et al.;An integrated process for the production of chemicals from biologically derived succinic acid; ACS Symposium Series, 2001, vol. 748, pp. 160-173. (abstract only).

(Continued)

*Primary Examiner* — Rei-tsang Shiao
(74) *Attorney, Agent, or Firm* — Wells St. John P.S.

(57) ABSTRACT

The invention includes methods of processing an initial di-carbonyl compound by conversion to a cyclic compound. The cyclic compound is reacted with an alkylating agent to form a derivative having an alkylated ring nitrogen. The invention encompasses a method of producing an N-alkyl product. Ammonia content of a solution is adjusted to produce a ratio of ammonia to di-carboxylate compound of from about 1:1 to about 1.5:1. An alkylating agent is added and the initial compound is alkylated and cyclized. The invention includes methods of making N-methyl pyrrolidinone (NMP). Aqueous ammonia and succinate is introduced into a vessel and ammonia is adjusted to provide a ratio of ammonia to succinate of less than 2:1. A methylating agent is reacted with succinate at a temperature of from greater than 100° C. to about 400° C. to produce N-methyl succinimide which is purified and hydrogenated to form NMP.

11 Claims, 2 Drawing Sheets

U.S. PATENT DOCUMENTS

| | | | |
|---|---|---|---|
| 5,434,273 | A | 7/1995 | Weyer et al. |
| 5,478,950 | A | 12/1995 | Bergfeld et al. |
| 5,508,396 | A | 4/1996 | Steffen |
| 5,536,849 | A | 7/1996 | Bergfeld et al. |
| 5,847,213 | A | 12/1998 | Kurusu et al. |
| 5,912,358 | A | 6/1999 | Frohn et al. |
| 6,008,375 | A | 12/1999 | Bergfeld et al. |
| 6,075,153 | A | 6/2000 | Bergfeld et al. |
| 6,248,902 | B1 | 6/2001 | Bertola |
| 6,348,601 | B2 | 2/2002 | Ohlbach et al. |
| 6,350,883 | B1 | 2/2002 | Chen et al. |
| 6,429,316 | B1 | 8/2002 | Takahashi et al. |
| 6,603,021 | B2 | 8/2003 | Werpy et al. |
| 6,632,951 | B2 | 10/2003 | Werpy et al. |
| 6,670,483 | B2 | 12/2003 | Werpy et al. |
| 6,706,893 | B2 | 3/2004 | Werpy et al. |
| 682,827 | A1 | 12/2004 | Manzer |
| 691,684 | A1 | 7/2005 | Manzer |
| 7,199,250 | B2 * | 4/2007 | Werpy et al. ............ 548/552 |
| 7,674,916 | B2 * | 3/2010 | Werpy et al. ............ 548/552 |
| 7,973,177 | B2 * | 7/2011 | Werpy et al. ............ 548/552 |

FOREIGN PATENT DOCUMENTS

| | | |
|---|---|---|
| EP | 632030 | 1/1995 |
| EP | 1201652 | 5/2002 |
| EP | 100044296 | 6/2010 |
| EP | 100044304 | 6/2010 |
| EP | 100044312 | 6/2010 |
| EP | 100753862 | 11/2010 |
| EP | 100753896 | 11/2010 |
| EP | 100753904 | 11/2010 |
| JP | 42023344 | 11/1967 |
| JP | 47018751 | 5/1972 |
| JP | 47021420 | 6/1972 |
| JP | 47027975 | 10/1972 |
| JP | 49000259 | 1/1974 |
| JP | 49020582 | 5/1974 |
| JP | 49020585 | 5/1974 |
| JP | 49020586 | 5/1974 |
| JP | 49048432 | 12/1974 |
| JP | 51016657 | 2/1976 |
| JP | 51042107 | 11/1976 |
| JP | 62120360 | 6/1987 |
| JP | 62289557 | 12/1987 |
| JP | 63027476 | 2/1988 |
| JP | 01186863 | 7/1989 |
| JP | 01186864 | 7/1989 |
| JP | 01190667 | 7/1989 |
| JP | 03081261 | 4/1991 |
| JP | 10158238 | 6/1998 |
| JP | 11349566 | 12/1999 |
| JP | 2000256312 | 9/2000 |
| JP | 2001002638 | 1/2001 |
| JP | 2001002640 | 1/2001 |
| JP | 2001114760 | 4/2001 |
| JP | 2001302626 | 10/2001 |
| JP | 2001354646 | 12/2001 |
| JP | 2001354647 | 12/2001 |
| RO | 96953 | 5/1989 |
| RO | 111189 | 7/1996 |
| RO | 113640 | 9/1998 |
| RU | 259889 | 12/1969 |
| RU | 619484 | 8/1978 |
| RU | 1558903 | 4/1990 |
| RU | 1735283 | 5/1992 |
| RU | 1753284 | 5/1992 |
| WO | WO 0130755 | 5/2001 |
| WO | PCT/US02/19372 | 9/2002 |
| WO | WO 02/083635 A1 | 10/2002 |
| WO | WO 02/102772 A1 | 12/2002 |
| WO | PCT/US02/19372 | 1/2003 |
| WO | WO 03/051868 A1 | 6/2003 |
| WO | PCT/US03/40106 | 5/2004 |

OTHER PUBLICATIONS

Subba Rao et al., "Synthesis of five-membered heterocycles over modified ZSM-5 catalysts", Catalysis: Modern Trends, Dec. 1994, pp. 110-113. (abstract only).

Miyajima, "Manufacturing process for N-methyl pyrrolidone", Chem. Econ. Eng. Rev., 1971, vol. 3(10), pp. 29-31. (abstract only).

Castiglioni et al.; Gamma-Butyrolactone for production of solvents with low environmental impact; Chimica e l'Industria (Milan), 1996, vol. 78(5), pp. 575-581. (abstract only).

Ershler et a\., "Electroreduction of N-methylsuccinimide to N-methylpyrrolidone", Elektrokhimiya, 1979, vol. 15(4), pp. 520-526. (abstract only).

Yu et al., "Production and application of N-methyl-2-pyrrolidone", Henan Huagong, 1999, vol. 7, pp. 10-12. (abstract only).

Takahata et al., "N-Alkylation of lactams with phase transfer catalyst", Heterocycles, 1979, vol. 12(11), pp. 1449-1451. (abstract only).

Auerbach et al., "N-Methylation of amides, lactams, and ureas", Journal Org. Chem., 1976, vol. 41(4), pp. 725-726. (abstract only).

Subba Rao et al., Modified ZSM-5 Catalysts for the Synthesis of Five and Six-Membered Heterocyclic Compounds, Journal of Organic Chemistry, 1994, vol. 59(14), pp. 3998-4000.

Kukalenko et al., "New synthesis of N-aryl and N-alkylpyrrolidones, and some of their properties", Khim. Geterotsikl. Soedin., 1971, vol. 7(6), pp. 773-774. (abstract only).

Anonymous, "Process for the isomerization of 4-methylannino-2-buten-1-ol to N-methylpyrrolidinone", Research Disclosure, 1993. (abstract only).

Sojka et al., "Problems in preparation of 2-pyrrolidinone and N-methylpyrrolidinone", Ropa a Uhlie, 1985, pp. 400-410. (abstract only).

Xue et al., "Studies on N-methyl-alpha-pyrrolidone synthesis", Shanghai Huagong, 1996, pp. 10-14. (abstract only).

Qiu et al., "Synthesis of N-methyl-2-pyrrolidone in vapor phase in the presence of catalysts" Shiyou Huagong, 1996, pp. 179-182. (abstract only).

Yan, "Preparation of 1-methyl-2-pynolidone by electrochemical method", Tianranqi Huagong, 2000, pp. 44-46. (abstract only).

Yano, "N-methyl-2-pyrrolidone", Yuki Gosei Kagaku Kyokaishi, 1983, pp. 880-881. (abstract only).

Cerveny et al. CAS Abstract 125:141930, (1996); 61(5), 764-769.

Stamboliyska et al;IP spectra and structure of 2.5-pyrrolidinedione(succinimide)and of its nitration:experimental and ab initio MO studies;Jnl of Mol. Struc. 516;2000;p. 237-45.

Cen et al., "N-alkylation of amides, imides, and lactams under phase-transfer catalysis", Zhongguo Yiyao Gongye Zazhi, 1990, pp. 218-220. (abstract only).

* cited by examiner

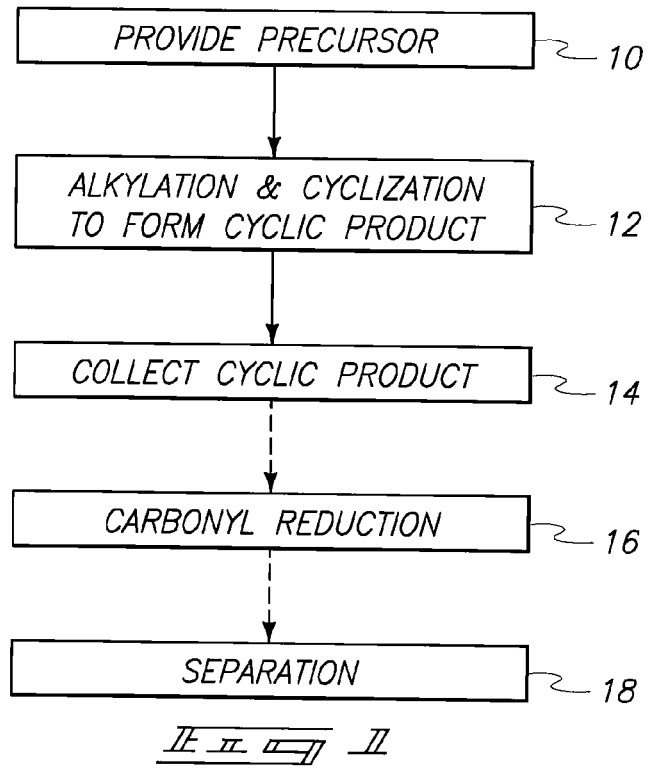
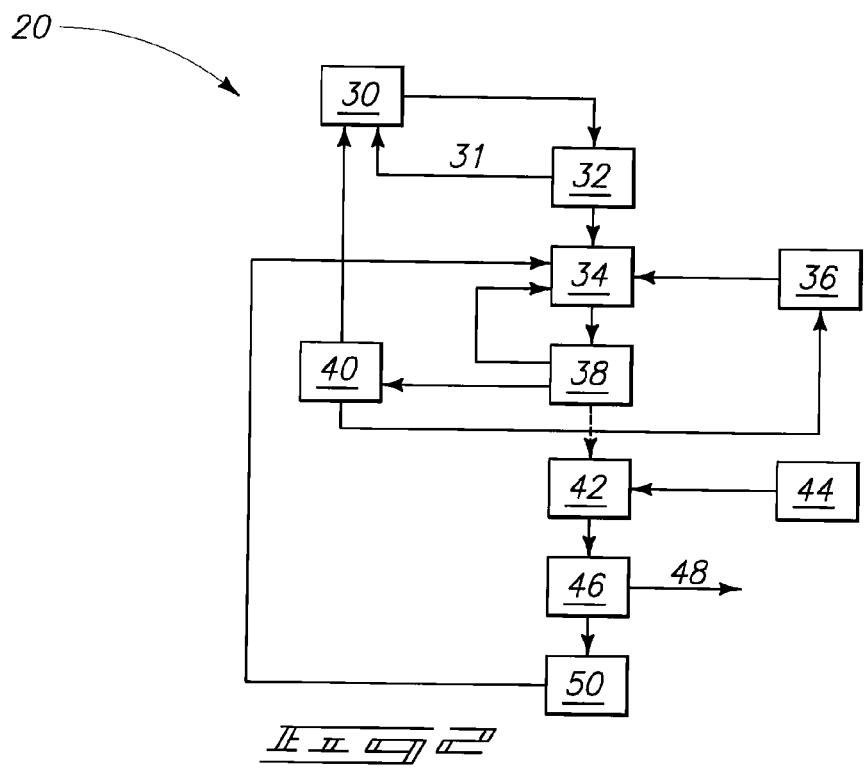

PROCESS FOR PRODUCING CYCLIC COMPOUNDS

RELATED PATENT DATA

This patent resulted from a divisional of U.S. patent application Ser. No. 12/702,818 filed on Feb. 9, 2010, now U.S. Pat. No. 7,973,177, which will issue Jul. 5, 2011, which is a divisional application of U.S. patent application Ser. No. 11/688,022 filed on Mar. 19, 2007, now issued as a U.S. Pat. No. 7,674,916, and which is a divisional of U.S. patent application Ser. No. 10/731,108 filed Dec. 10, 2003, now issued as U.S. Pat. No. 7,199,250, which claims benefit of priority under 35 U.S.C. §119 to U.S. Provisional Patent Ser. No. 60/435,469, which was filed Dec. 20, 2002, all of which are incorporated herein by reference.

TECHNICAL FIELD

The invention pertains to methods of processing di-carbonyl compounds, methods of producing cyclic compounds comprising a heteroatom ring member, including N-alkyl succinimide, and methods of producing pyrrolidinones.

BACKGROUND OF THE INVENTION

Cyclic compounds such as pyrrolidinones, N-substituted pyrrolidinones, other cyclic amines, and other cyclic compounds having one or more hetero-atom ring members, are useful as solvents, anti-fungal agents, pesticides, herbicides, anticorrosion agents, antioxidants, UV protectants, for use in forming polymers and plastics, and as reagents for forming other useful compounds. Conventional methods of forming these compounds can be expensive and inefficient. It would be desirable to develop processes for production of cyclic amines and other cyclic compounds.

SUMMARY OF THE INVENTION

In one aspect the invention encompasses a method of processing an initial di-carbonyl compound. The initial compound is converted to a cyclic compound having a ring nitrogen atom and two carbonyl groups. The cyclic compound is reacted with an alkylating agent to form a derivative having an alkylated ring nitrogen. The alkylated cyclic compound is produced in a mixture containing additional components and a purification process is performed to remove at least some of the additional components.

In one aspect the invention encompasses a method of producing an N-alkyl product. An initial solution is provided to a reactor, the initial solution comprises a di-carboxylate compound and ammonia, where the ratio of ammonia to the di-carboxylate compound is from 0:1 to greater than 2:1. For purposes of the description, when referring to a solution or mixture the term ammonia is intended to encompass either or both $NH_3$ and $NH_4^+$, unless specifically indicated otherwise. The amount of ammonia in solution is adjusted to produce a solution having a second ratio of ammonia to di-carboxylate compound of from about 1:1 to about 1.5:1. An alkylating agent is added to the solution having the second ratio and the initial compound is alkylated and cyclized to produce a cyclic N-alkyl product.

In one aspect the invention encompasses a method of making N-methyl pyrrolidinone. An aqueous mixture comprising ammonia and succinate is introduced into a vessel. The amount of ammonia in the aqueous mixture is adjusted to provide a ratio of ammonia to succinate of from about 1:1 to less than about 2:1. A methylating agent is introduced into the vessel and is reacted with succinate at a temperature of from greater than 100° C. to about 400° C. to produce N-methyl succinimide. The N-methyl succinimide is at least partially purified and is subsequently hydrogenated to form a product mixture comprising N-methyl pyrrolidinone.

BRIEF DESCRIPTION OF THE DRAWINGS

Preferred embodiments of the invention are described below with reference to the following accompanying drawings.

FIG. 1 is a block-diagram flowchart view of a generalized method encompassed by the present invention.

FIG. 3 is an illustration of potential equilibrium reactions that can occur in a particular aspect of the invention.

DETAILED DESCRIPTION OF THE PREFERRED EMBODIMENTS

Figure 2:
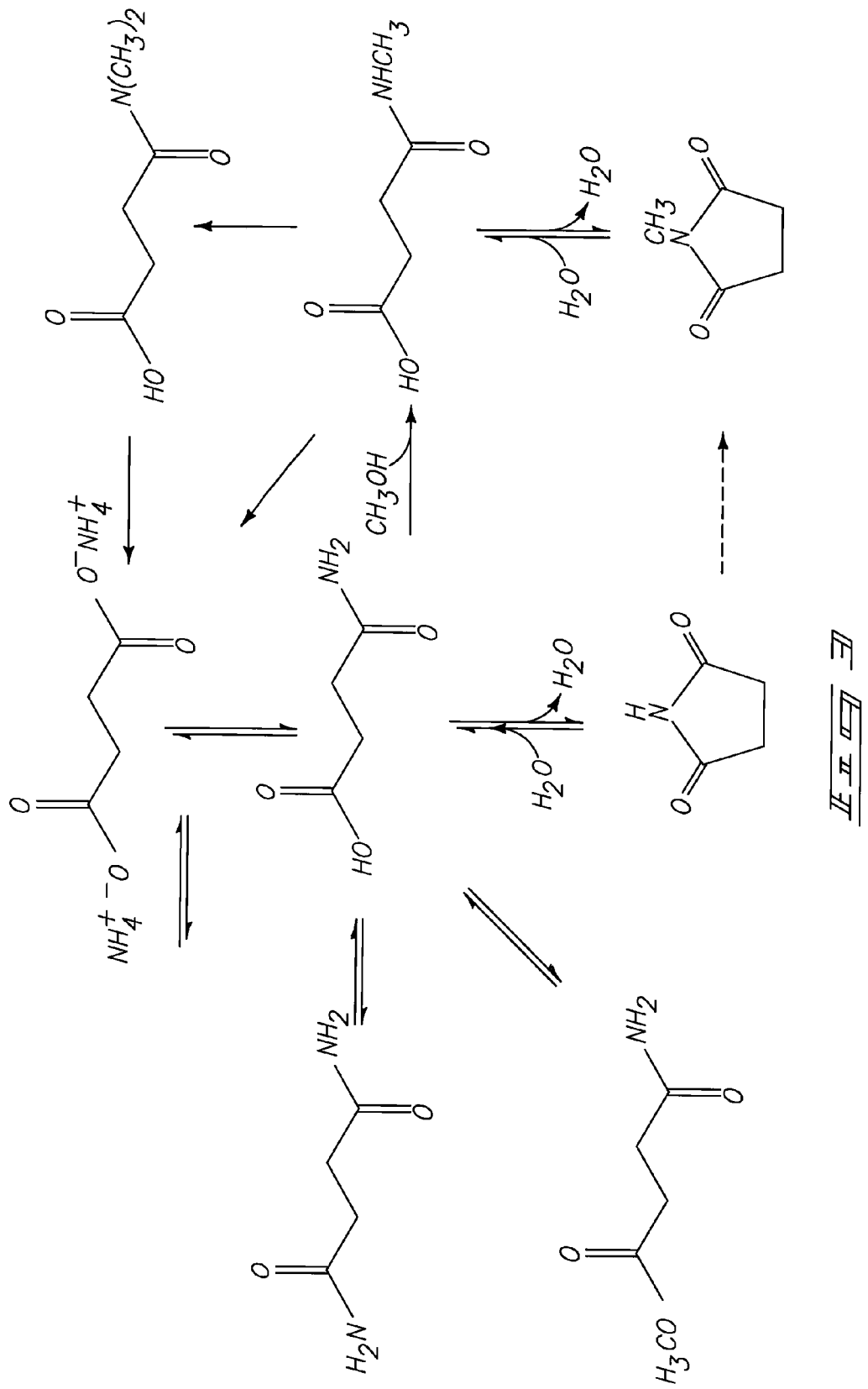
FIG. 2 is a process flow diagram showing a processing system that can be used in performing particular aspects of the present invention.

This disclosure of the invention is submitted in furtherance of the constitutional purposes of the U.S. Patent Laws "to promote the progress of science and useful arts" (Article 1, Section 8).

In general, methods according to the present invention can be utilized to produce a cyclic nitrogen-comprising compound having formula (I), Formula (I):

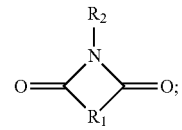

where $R_1$ is a linear or branched, saturated or unsaturated hydrocarbon or substituted hydrocarbon. Preferably, $R_1$ contains twenty or fewer non-hydrogen atoms, and in particular instances can preferably comprise from 1-10 carbon atoms. Alternatively, $R_1$ can be absent such that the resulting product is a three membered nitrogen comprising ring compound. $R_2$ can be an alkyl (linear, cyclic or branched, saturated or unsaturated), a substituted alkyl group, an aromatic group or hydrogen.

$R_1$ can preferably be a branched or un-branched, saturated or unsaturated, substituted or non-substituted group which allows the ring structure of formula (I) to be a 5-, 6- or 7-membered ring. In particular instances, the formula (I) compound can have one of the 5- or 6-membered ring formulas shown in Table 1, where $R_3$ through $R_8$ are not limited to any particular groups, and can be independently selected from hydrogen, hydroxyl, hetero-atom comprising functional groups, linear or branched groups, and saturated or unsaturated groups, including hydrocarbon groups or substituted hydrocarbons.

TABLE 1

Example Formula (I) Compounds

| 5-member ring compounds | 6-member ring compounds |
|---|---|

TABLE 1-continued

Example Formula (I) Compounds

| 5-member ring compounds | 6-member ring compounds |
|---|---|
| | |
| | |
| | |
| | |

The product having formula (I) can optionally undergo further derivatization in accordance with a second aspect of the invention to produce a compound having formula (II).

Formula (II):

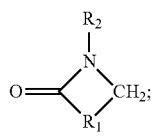

where $R_2$ is any of the substituents set forth above with respect to $R_2$, and $R_1$ is any of the groups indicated above with respect to $R_1$. The invention also contemplates three membered ring compounds analogous to the formula II compound where $R_1$ is absent. The invention can be particularly useful for production of N-methyl succinimide (NMS), a formula I compound, which in accordance with the second aspect of the invention can optionally be utilized for production of N-methyl pyrrolidinone, ((NMP), also known as N-methyl pyrrolidone).

For simplicity of description, the various methods and aspects of the invention will be described in terms of production of NMS and/or NMP. However, it is to be understood that the described methods and aspects can be adapted for production of any of the compounds having formula (I) or (II) set forth above.

Methods encompassed by the present invention are described generally with reference to FIGS. 1-2. Referring initially to FIG. 1, a precursor compound can be provided in an initial step 10. The precursor provided in step 10 can comprise a compound having formula (III).

Formula (III):

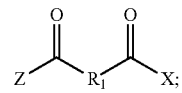

where Z and X independently comprise one or more C, H, O, N, S, a halide, and a counter-ion. In particular instances one or both of Z and X can be selected from OH, OR, and O⁻ (free or with a counterion). $R_1$ can be any of the groups set forth above with respect to $R_1$. Alternatively, the precursor can be a compound analogous to formula (III) where $R_1$ is absent.

In particular embodiments, the initial compound utilized in process 10 can be succinic acid or a succinic acid derivative such as, for example, a monoester, a diester, succinate, succinamic acid, a succinamic ester, succinamide, and N-alkylated succinimide, a substituted succinic acid (e.g. itaconic acid) or a succinate salt. Where a succinate salt is utilized, the counter-ion is not limited to a particular species and in some aspects can preferably be ammonium. Alternatively, the precursor provided in step 10 can be one of the following acids or a derivative thereof: fumaric, itaconic, malic, maleic, aspartic, citric and glutamic.

The process of providing the precursor can preferably comprise forming an aqueous mixture containing the desired precursor. In particular instances, process 10 can include a fermentation process where the precursor is a fermentation product. For purposes of the description, methods of the present invention will be further described utilizing succinic acid or a derivative thereof as an exemplary starting material for utilization in process 10. Such can be produced by fermentation and in particular instances can be provided in process 10 in a fermentation broth (where fermentation broth refers to an aqueous mixture having some or all of the components present in the fermentation reaction retained in the mixture). It is to be understood that the methods can also utilize succinic acid derivatives or other precursor compounds produced by means other than fermentation.

Where succinate is provided as the precursor, such can preferably be provided as ammonium succinate in an aqueous mixture or aqueous solution. For purposes of the description that follows, all ratios refer to mole ratios unless otherwise indicated, and all percents are based upon weight unless otherwise indicated. Where a fermentation process is utilized to produce the succinate, an initial fermentation broth can in particular instances comprise a ratio of ammonia to succinate of from less than 1:1 to greater than or equal to 2:1. Further, the fermentation broth can comprise from about 3-30% ammonia succinate by weight relative to the total weight of the mixture (after filtration removal of cellular components; see below). Optionally, the amount of water can be reduced in the mixture by performing a concentration step. The concentration step can produce a solid form of ammonium succinate, or can produce a mixture of ammonia and succinate in water. Where a mixture is produced, the mixture can have from about 10% to about 80% of ammonium succinate (or ammonia and succinate) by weight, preferably approximately 50%.

Process 10 can optionally comprise adjustment of the ammonia content of the mixture. Where succinate is produced by a fermentation process, the adjustment can provide a final ammonia to succinate ratio of less than 2:1. Preferably, the final ammonia to succinate ratio will be less than about 1.8:1, more preferably from about 1:1 to about 1.5:1, and most preferably will be between 1.2:1 and 1.4:1. Such adjustment can comprise, for example, removal of ammonia.

Alternatively, where process 10 does not comprise a fermentation process or where succinate is provided in a nonammonia form, ammonia can be added to the mixture in step 10 to provide the desired ratio of ammonia to succinate. It can be advantageous to provide an ammonia to succinate ratio of less than 2:1 in the mixture to optimize the subsequent reaction performed in process 12 (discussed below).

Where process 10 involves fermentation, the fermentation broth produced during fermentation can optionally undergo a filtration step to remove cells and/or at least some cellular components present in the fermentation broth prior to reaction step 12. It is to be noted, however, that the filtration is optional. Accordingly, in certain instances a reaction broth can be provided to step 12 without being subjected to any of the filtration, concentration or ammonia adjustment steps discussed above. It is to be understood that the invention encompasses utilization of none or any combination of the ammonia adjustment, succinate concentration and fermentation broth filtration steps described.

The precursor provided in process 10 can be subjected to an alkylation and cyclization process 12 to form a cyclic product as shown in FIG. 1. The alkylation and cyclization of process 12 can be conducted concurrently, or cyclization can be followed by alkylation. For purposes of the description, where alkylation and cyclization are conducted concurrently, no reaction sequence or mechanism is implied. The reaction process 12 can be conducted under thermal conditions in the absence of any added catalyst or can alternatively be conducted in the presence of a catalyst, such as an acidic catalyst. Thermal conditions utilized in producing the cyclic compound in process 12 preferably utilize a temperature of from at least 100° C. to about 400° C. In particular instances the thermal conditions utilize a temperature of between 100° C. and 300° C. It is to be understood that the invention also encompasses producing non-alkylated cyclic compounds, and accordingly, the described conditions can be utilized in an absence of addition of alkylating agent.

Process 12 can comprise thermal cyclization of at least some of the precursor prior to addition of any alkylating agent or can comprise addition of an alkylating agent prior to or at initiation of the cyclization reaction. The alkylating agent provided to process 12 is not limited to a particular reagent and can be any alkylating agent to produce the desired $R_2$ group. Exemplary alkylating agents appropriate for process 12 include, but are not limited to, an alcohol, a glycol, a polyol, an epoxide and aziridine, urea, an acetal, a thiol, a carboxylate, an alkyl halide, an alkyl amine, a carbonate compound, a thiol compound, a thiol-carbonate compound, a sulfate compound and mixtures thereof. In particular instances, it can be preferable to utilize an alcohol as the alkylating reagent. The alcohol can be provided at, for example, a ratio of from about 1:1 to about 30:1 relative to the succinate or alternative precursor. A preferable ratio of alcohol to precursor can be from 1:1 to about 10:1. For instance, where the desired product is NMS, methanol can be added to the reaction such that at initiation the reaction has a methanol to succinate ratio of from about 1:1 to about 10:1. In particular instances, the methanol to succinate can preferably be from about 1:1 to about 3:1, and more preferably from about 1.5:1 to about 2:1.

Reaction process 12 can optionally include an immediate quench cooling or flash cooling. An exemplary quench cooling process can comprise cooling from the reaction temperature to below 100° C. in a time of less than or equal to about 30 minutes. It can be advantageous to quench or flash cool the reaction mixture to inhibit ring opening and to maximize yield of the cyclic alkylated product. The processing of step 12 can be utilized to form, for example, compounds of formula (I) discussed above.

The cyclic alkylated compound produced in process 12 can optionally be collected in a collection process 14 as shown in FIG. 1. It is to be understood that in some instances, such as where the cyclic alkylated compound will undergo further conversion or derivatization, the collection step may be omitted. Collection process 14 at least partially purifies the cyclic alkylated products by removing at least some of any potentially detrimental fermentation broth components, alkylating agents and/or byproducts produced during process 12. For purification purposes it can be advantageous that $R_2$ be a group which confers or enhances properties useful in purification such as volatility, hydrophobicity, etc. Alternative purification methods appropriate for process step 14 include but are not limited to distillation, sublimation, decanting, steam distillation, extraction and crystallization. Successive purification steps can be utilized to improve product purity. In particular instances, it can be preferable that a compound of formula (I) produced in step 12 be volatile to allow separation by distillation. In instances where the cyclic product will be further processed in accordance with aspects of the invention, it can be advantageous to utilize a distillation process for purification. Where subsequent processing is to be conducted under thermal conditions, the distillation product can be directly provided to the downstream process without an intervening cooling step.

Although the reaction and distillation is described above as occurring independently, it is to be understood that the invention additionally encompasses concurrent reacting to form the cyclic product (whether it be alkylated or non-alkylated), and purification of such product as it is formed. For example, concurrent reaction and purification can be conducted by reactive distillation.

As indicated above, cyclization and alkylation process 12 can optionally be conducted in the presence of components of a fermentation broth. However, it can be advantageous to purify the product compound having formula (I) prior to any subsequent processing in order to avoid detrimental effects upon any catalyst which may be utilized during the subsequent processing.

The compound of formula (I) collected and/or partially purified in process 14 can be further processed by carbonyl reduction process 16 or can alternatively be utilized to form other useful products (not shown). Carbonyl reduction processing 16 can comprise hydrogenation of the formula (I) compound to produce one or more of a compound having a formula (II), a compound having a formula (IV), a compound having a formula (V), and a compound having formula (VI).

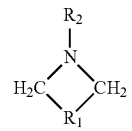

Formula (IV)

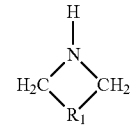

Formula (V)

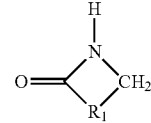

Formula (VI)

Preferably, where two or more of formulas (II), (IV), (V) and (VI) are produced in a product mixture in process 16, compound formula (II) is the majority product. More preferably compound of formula (II) is selectively produced relative to each of the other three products. In particular instances the product mixture can comprise at least 90% compound (II).

Carbonyl reduction process 16 can utilize a reduction catalyst in the presence of hydrogen. Although the description emphasizes selective production of a compound of formula (II), it is to be understood that the invention encompasses selective production of any of the compounds having formulas (IV, V and VI). Conversion efficiency and/or selectivity can be dependent upon various conditions utilized in process 16 including, for example, the specific catalysts utilized, purity of the starting material, length of exposure to the catalyst, hydrogen pressure, reaction temperature, the amount of water present (if any), etc. Appropriate catalysts for utilization in process 16 can preferably comprise one or more of Fe, Ni, Pd, Pt, Co, Sn, Rh, Re, Ir, Os, Au, Ru, Zr, Ag and Cu. The catalyst can additionally comprise a support such as for example a porous carbon support, a metallic support, a metallic oxide support or mixtures thereof. In particular instances the catalyst can contain a catalytic metal on a support containing both metal oxide and carbon. For purposes of the invention, the carbon support can be a granular carbon or carbon powder and in particular instances, the catalytic metal (s) can be edge-coated onto the carbon support.

In instances where the compound having formula (I) collected in process 14 is NMS, and selective production of NMP in process 16 is desired, the hydrogenation catalyst utilized can preferably comprise one or more of Re, Rh, Zr, Ni, Ru, Pt, Pd and Co. Particularly useful catalysts for selective production of NMP are listed in Table 2, along with the commercial source where appropriate.

TABLE 2

Conversion catalysts

| Source | Catalyst Number | Description |
| --- | --- | --- |
| Synthesized | 1 | 2.5% Re on Calgon 120 CTC granular C (uniform metal distribution) |
| Synthesized | 2 | 2.5% Rh 2.5% Zr on Calgon 120 CTC C (mixed metal distribution) |
| Synthesized | 3 | 2.5% Ni 2.5% Re on Norit ROX 0.8 mm C extrudate (Uniform metal distribution) |
| Synthesized | 4 | 2.5% Rh 2.5% Re on Norit ROX 0.8 mm C extrudate (Uniform metal distribution) |
| *Engelhard Corp. | 6757-09-1 | 2.5% Ru on PICA 12 × 20 mesh granular C |
| *Engelhard Corp. | ESCAT 268 | 5% Pt on C powder (uniform metal distribution; pre-reduced; water-wet) |
| *Engelhard Corp. | ESCAT 340 | 5% Rh on C powder (mixed-metal distribution; pre-reduced; water-wet) |
| *Engelhard Corp. | ESCAT 140 | 5% Pd on C powder (mixed-metal distribution; pre-reduced; water-wet) |
| *Engelhard Corp. | ESCAT 440 | 5% Ru on C powder (mixed-metal distribution; pre-reduced; water-wet) |
| *Engelhard Corp. | Co-0138 E 1/16 3F | ~30% Co on 3-finned alumina extrudate (dry; pre-reduced; passivated) |
| **Degussa Corp. | G 106 B/W 5% Rh | 5% Rh on C powder (pre-reduced; water wet) |

*Engelhard Corporation, Iselin, New Jersey;
**Degussa, Germany

In instances where NMS produced in step 14 is utilized for production of NMP, efficiency and selectivity can be enhanced by performing hydrogenation process 16 in the presence of no water or very little water (for example less, than or equal to about 10%, by weight). Accordingly, it can be preferable to provide the product of process 14 to reduction reaction 16 in solid or molten form. Further, the formula (I) compound can be provided to process 16 in molten form directly from any high temperature purification step performed in process 14 and thus increase time efficiency by avoiding an additional cooling step.

An appropriate reaction temperature for conversion of NMS in process 16 can be from about 120° C. to about 220° C. Alternative temperatures can be utilized for alternative conversion/hydrogenation reactions.

Utilization of the above conditions for reduction process 16 typically results in a product mixture containing very little, if any, of products having formula's (IV) or (V). In other words, products of formula (II and VI) are typically the primary products produced during step 16. Compounds having formula (II and IV) can be separated from other reaction components, any products (IV) and (V) present and can optionally be separated relative to each other in separation process 18. Compound having formula (II) can be separated from other components in the mixture using, for example, one or more of distillation, crystallization, ion exchange and selective adsorption.

Referring to FIG. 2, a system 20 is shown which can be utilized in particular aspects of the invention for producing a compound having formula (I) and/or a compound having formula (II). Although system 20 is described below relative to production of NMS and/or NMP, it is to be understood that system 20 can be adapted for production of alternative formula (I) compounds and/or formula (II) compounds utilizing alternative reagents as set forth above.

A succinic acid derivative can be provided from a source 30 into an initial process reactor 32. Source 30 can be, for example, a fermentation processor where the fermentation produces succinate.

Where source 30 comprises fermentation, such fermentation can be performed in corn steep liquor with added glucose and ammonia. At least some of the glucose and ammonia are converted into diammonium and/or ammonium succinate. The succinate fermentation product can be provided directly to reactor 32 in the original state of the fermentation broth. Alternatively, the fermentation broth can be filtered to remove cells and/or cellular components prior to introduction into reactor 32. A typical succinate concentration of an original fermentation broth (after filtration) can be from about 3% to about 30%, by weight. The succinate can be concentrated prior to or after providing it to reactor 32, and can preferably be concentrated to comprise a final succinate concentration of approximately 50%. Water can be recovered during the concentration step and recycled along recycle route 31 back to source 30.

An initial ammonia content of the fermentation broth can be adjusted in reactor 32. Such adjustment can comprise removal of ammonia from reactor 32. Ammonia-removal can be conducted at a temperature of from about 130° C. to about 200° C. The ammonia can be recovered and recycled along recycle route 31 to source 30. The removal of ammonia can be utilized to produce a final preferable ammonia to succinate ratio of between 1.2 and 1.4.

As shown in FIG. 2, the resulting ammonia adjusted mixture can be provided into a second reactor 34 for further reaction. Alternatively, reagents can be added to reactor 32 for further reaction processes (not shown). The mixture containing succinate provided to reactor 34 can be added to reactor 34 prior to, after, or simultaneous to addition of alkylating agent from a reagent source 36, and alkylation and cyclization can be conducted concurrently. Alternatively, the succinate can be cyclized in reactor 34 prior to addition of any alkylating agent. NMS can be produced in reaction chamber 34 by addition of a methylating agent such as, for example, methanol. Where methanol is utilized in producing NMS in reactor 34, the methanol can be added to reactor 34 at a methanol to succinate ratio of from 1 to about 30. Preferably, methanol is added to a ratio of from about 1.5:1 to about 3:1, relative to succinate. In particular instances, it can be preferable to provide a methanol to succinate ratio of about 2:1.

Conversion to NMS can be performed under thermal conditions without additional catalysts. Alternatively, a catalyst can be added to reactor 34. An exemplary catalyst for addition to reactor 34 is an acidic catalyst.

Conversion to NMS in reactor 34 can be conducted at a reaction temperature of from above about 100° C. to about 300° C., preferably about 280° C. An appropriate reaction temperature can depend upon the amount of water present, with an increased temperature enhancing efficiency at higher water content.

Various equilibrium reactions can occur within reactor 34. Exemplary potential equilibrium reactions are shown generally in FIG. 3. The equilibrium positions are not indicated in FIG. 3, and can be affected by various factors such as reactant concentration, water content, and ammonia to succinate ratio. Due to the reversibility of the ring closure, it can be advantageous to quench or flash cool the conversion reaction. Quenching can comprise, for example, cooling the reaction to a temperature below 100° C. in less than or equal to about 30 minutes. Such quenching or flash cooling can maximize the ring closed NMS.

The NMS produced in reactor 34 can be recovered in reactor 38. Reactor 38 can be, for example, a distillation unit for separation of NMS from byproducts including, for example, polymerized material and/or various equilibrium products shown in FIG. 3. Such distillation can also be utilized to remove fermentation broth components. Polymerized material and/or equilibrium products of FIG. 3 can be recovered from reactor 38 and can be recycled back to reactor 34 for production of an additional amount of NMS. Methanol and/or water can also be recovered from reactor 38 and can optionally undergo separation of water from methanol in, for example, a distillation reactor 40 where water can be recycled back to source 30 and methanol can recycle back to alkylating agent source 36. Nitrogen-containing byproducts such as, for example, methyl amine can also be recovered and separated in distillation reactor 40 for recycling back to reactor 34.

In addition to the distillation discussed above, purification of NMS in reactor 38 can alternatively comprise one or more of steam distillation, decanting, sublimation, extraction and crystallization. In particular instances, purification of NMS can be conducted as NMS is formed. For example, a single reactor (not shown) can be utilized for conducting the reaction to form NMS and for purification of the NMS. A particularly useful combination reactor can be, for example, a distillation reactor.

The purified NMS can be provided to reactor 42 to undergo further reaction or can be utilized for production of alternative useful compounds. It can be advantageous to purify NMS prior to introducing the NMS into reactor 42 to avoid catalyst poisoning or other negative effects of mixture components from reactor 34. Such purification is especially beneficial where a fermentation broth is utilized since components of the fermentation broth can decrease or destroy catalytic activity.

It is noted that under appropriate distillation conditions in reactor 38, an amount of NMS recovered from reactor 38 can exceed the initial amount of NMS fed to the reactor. This result is likely due to conversion of one or more of the equilibrium products shown in FIG. 3, which occurs during distillation purification of NMS. An exemplary conversion of equilibrium product which may occur during distillation is conversion of N-methyl succinamic acid to produce NMS and water.

Hydrogenation of NMS can be performed in reactor 42 in the presence of a hydrogenation catalyst. Hydrogen can be provided into reactor 42 from a hydrogen source 44. The hydrogenation catalyst utilized can be any of the hydrogenation catalysts set forth above. Preferably, the catalyst will comprise from about 0.5% to about 5% catalytic metal by weight, and such metal will be on a carbon support. In particular instances, the catalyst will preferably comprise one or more of Ru, Rh and Pt since these catalytic metals can enhance conversion from NMS and can enhance selectivity to NMP. For highly selective and efficient production of NMP, the catalysts can preferably comprise up to about 5% Rh on a carbon support, and can preferably be an edge-coated catalyst.

Additional factors which can affect NMS conversion efficiency and selectivity toward NMP include, but are not limited to, reaction temperature, hydrogen pressure, initial NMS concentration, catalyst loading, stirring rate, reactor residence time, and the reaction solvent. Due to hydrogen's limited solubility in aqueous media, it can be preferable that the NMS be converted in an absence of water or in the presence of very little water. Accordingly, it can be desirable to provide neat NMS or an NMS in a mixture comprising less than or equal to 80% water, preferably less than or equal to 50% water, more preferably less than or equal to about 20% water, and even more preferable less than or equal to about 10% water.

Hydrogenation in reactor 42 can preferably comprise a $H_2$ pressure of from about 500 psig to about 2250 psig. It can be advantageous in particular instances to provide a $H_2$ pressure of up to about 1500 psig to minimize production of pyrrolidines. Where NMS is hydrogenated in an absence of solvent, an appropriate reaction temperature can be from at least 70° C. to less than or equal to about 250° C. Where solvent is utilized, an appropriate reaction temperature can preferably be less than or equal to about 250° C.

Conversion of NMS in reactor 42 can result in a product mixture comprising NMP, 2-pyrrolidinone, pyrrolidine, and methylpyrrolidine. The reaction can also produce byproducts such as amines and polymerized material. The resulting mixture from reactor 42 can be introduced into reactor 46 where over-hydrogenated products such as pyrrolidines, amines, and other hydrocarbons (reaction "lights") can be removed to waste 48 by flash removal. The remaining mixture from flash tank 46 can be provided into a reactor 50. Production of high purity NMP can be obtained by, for example, distilling in reactor 50. Alternatively, NMP purification can comprise one or more of crystallization, ion exchange, extraction and selective adsorption. Such purification can separate NMP from remaining methanol and water which can optionally be recycled, and from "heavies" such as any polymerized material and/or alternative equilibrium species shown in FIG. 3. Such "heavies" or equilibrium species can be recycled back to reactor 34 for additional NMS production. Purification in reactor 50 can additionally separate NMP from any 2-pyrrolidinone produced during the hydrogenation reaction.

It can be advantageous to include recycling of polymerized materials and/or alternative equilibrium species in accordance with the methods of the invention to improve the NMP at an overall percent yield of greater than 92% by mole, relative to the initial amount of succinate.

EXAMPLES

Example 1

N-Methyl Succinimide Formation in the Presence of Fermentation Components

Ammonium succinate (at a molar ratio of ammonia relative to succinate of 1.2:1) is provided to a reactor in a mixture containing corn steep liquor. The corn steep liquor contains approximately 10% non-water components prior to mixing with ammonium succinate. The mixture is formed to contain approximately 28% ammonium succinate, by weight. Methanol is provided at a methanol to succinate ratio of about 1.5:1. Conversion of ammonium succinate is conducted at 280° C. for 8 hrs. Multiple samples are drawn and results are analyzed to obtain conversion and selectivity information. Analysis after 8 hours indicates a succinate conversion of greater than or equal to 92.9%. The yield of N-methyl succinimide (NMS) is greater than or equal to 70%, with a corresponding production of less than 6.4% N-methyl succinamic acid, less than or equal to 1.7% succinamic acid, and less than 0.5% succinimide.

A comparison sample run is conducted utilizing conditions set forth above with the exception that the corn steep liquor is replaced with an equivalent amount of water (by weight). Analysis after 8 hours indicates a succinate conversion of 93.7%, with a corresponding 68.3% yield of NMS, 1.6% N-methyl succinamic acid, 3.4% succinamic acid, and 1.8% succinimide.

These results indicate that conversion of succinate to NMS can be efficiently performed in the presence of fermentation components.

Example 2

Ammonia Adjustment and Thermal Formation of Succinamic Acid from Diammonium Succinate

Diammonium succinate is provided to a reactor at 50 weight percent in water. The reactor is filled or pressurized with nitrogen and sealed. The sealed reactor is heated to about 200° C. and thereafter samples are collected from the reactor every 10 minutes. The samples are analyzed to determine conversion and selectivity. The results of such analysis are shown in Table 3.

TABLE 3

Diammonium Succinate Conversion and Product Selectivities

| Elapsed Minutes at 200° C. | Diammonium Succinate Conversion (%) | Selectivity to Succinamic Acid | Selectivity to Succinimide | Selectivity to succinamide |
|---|---|---|---|---|
| Feed | 0 | 0 | 0 | 0 |
| 0 | 21.6 | 84.3 | 10.5 | 5.2 |
| 10 | 41.7 | 78.4 | 11.8 | 9.8 |
| 20 | 56.8 | 74.7 | 11.9 | 13.4 |
| 30 | 62.7 | 73.2 | 11.7 | 15.1 |
| 40 | 64.8 | 72.7 | 11.9 | 15.4 |
| 50 | 65.3 | 73.9 | 11.2 | 14.9 |

The process can produce an ammonia to succinate ratio of about 1.4:1 which is within the preferable range for subsequent formation of N-methyl succinimide. The described method is useful for production of succinamic acid and/or succinimide which as a reagent can be utilized for enhanced NMS production relative to utilization of diammonium succinate.

Example 3

N-Methyl Succinimide Formation from Succinamic Acid

Succinamic acid is provided to a reactor at 30% by weight in water. Methanol is provided to the reactor at a 1.5:1 methanol to succinamic acid ratio, and ammonia is added to provide a 0.2:1 ammonia to succinamic acid ratio. This represents a 1.2:1 ammonia to succinate species ratio due to the ammonia integrated into the succinamic acid. The reactor is filled or pressurized with nitrogen and sealed. The reactor is heated to 280° C. and maintained at temperature for 10 hours before quench cooling. The product is analyzed to determine conversion and selectivity products. Analysis after 8 hours indicates a succinamic acid conversion of greater than or equal to 96.5%. The yield of N-methyl succinimide (NMS) is greater than or equal to 77%, with a corresponding production of less than 6.1% N-methyl succinamic acid, less than or equal to 5% succinic acid, and less than 1.7% succinimide.

Example 4

Ammonia Adjustment and Thermal Formation of Succinimide from Diammonium Succinate

Diammonium succinate is provided to a reactor at 50% by weight in water. The reactor is subjected to vacuum and water is distilled off at 50° C. to yield nearly 100% DAS. The reactor is returned to atmospheric pressure, filled or pressurized with nitrogen, and heated to the indicated temperature and held for the indicated time before cooling the reactor to room temperature. The product is weighed, dissolved in water, and analyzed to determine conversion and selectivity to intermediates. The overall mass balances are observed to be high but not above expected analytical tolerances.

TABLE 4

Diammonium Succinate Conversion and Product Selectivities

| Temp. (° C.) | Elapsed Time at Temp (min) | Diammonium Succinate Conversion (%) | Selectivity to Succinamic Acid | Selectivity to Succinimide | Selectivity to succindiamide |
|---|---|---|---|---|---|
| 200° C. to 270° C. | 30 | 93.9 | 4.6 | 93.8 | n/d |
| 200° C. | 60 | 90.8 | 5.0 | 96.5 | 1.5 |

TABLE 4-continued

Diammonium Succinate Conversion and Product Selectivities

| Temp. (° C.) | Elapsed Time at Temp (min) | Diammonium Succinate Conversion (%) | Selectivity to Succinamic Acid | Selectivity to Succinimide | Selectivity to succindiamide |
|---|---|---|---|---|---|
| 200° C. | 90 | 93.3 | 0.1 | 98.5 | n/d |
| 160° C. | 480 | 91.7 | 0.1 | 97.8 | n/d |
| 220° C. | 30 | 93.2 | 2.5 | 101.5 | n/d | n/d = not detected

This method forms succinimide with a release approximately half the original ammonia as the DAS cyclizes to form succinimide. The ammonia is removed in the vapor phase along with water. Accordingly, the process produces a nearly 1:1 ammonia to succinate ratio. However, the process can alternatively be stopped at any ratio between 1:1 to 2:1. This process forms mostly succinimide with some succinamic acid present, each of which can be favorable intermediates for converting to N-methyl succinimide.

Example 5

Formation of N-Methyl Succinimide from Succinimide

Succinimide is provided to a reactor at 23% by weight in water. Methanol is provided to the reactor at a 1.5:1 methanol to succinimide ratio in an absence of added ammonia. The ammonia integrated within the succinimide provides a 1:1 ammonia to succinate species ratio. The reactor is pressurized with nitrogen and sealed. The reactor is heated to 300° C. and is maintained at temperature for 5 hours. Samples are collected at least every hour during the reaction. Product analysis is conducted to determine conversion and product selectivity. Analysis of the 4 hour sample indicates a succinimide conversion of greater than or equal to 96%. The yield of N-methyl succinimide (NMS) is greater than or equal to 80%.

Example 6

N-Methyl Succinimide Hydrogenation

Approximately 5.0 grams (g) of the specified catalyst is charged into a reactor equipped with a magnetic stirrer. Approximately 50.0 g of solid NMS is utilized a feedstock and is provided to the reactor. The reaction is conducted under 1500 psig constant $H_2$ pressure at a stir rate of about 1000 rpm. After 4 hrs, the resulting gas and liquid components are analyzed for determination of NMS conversion and product selectivity. The results of the determinations are indicated in Table 5 for each of the indicated catalysts and reaction temperatures.

TABLE 5

Catalyst Based Hydrogenation Selectivities

| Catalyst No. (from Table 2) | Temp. (° C.) | % of NMS Converted | molar % (of theoretical) Yield of NMP | NMP/2-pyrrolidinone (Mole Ratio) |
|---|---|---|---|---|
| 1 | 200 | <1 | 0.6 | n/d |
| 2 | 200 | 7 | 6.8 | 25 |
| 3 | 200 | 3 | 3 | 10 |
| 4 | 200 | 65 | 55.9 | 65 |

TABLE 5-continued

Catalyst Based Hydrogenation Selectivities

| Catalyst No. (from Table 2) | Temp. (° C.) | % of NMS Converted | molar % (of theoretical) Yield of NMP | NMP/2-pyrrolidinone (Mole Ratio) |
|---|---|---|---|---|
| 6757-09-1 | 200 | 84 | 69.3 | 10 |
| ESCAT-268 | 200 | 26 | 25.7 | >90 |
| ESCAT-340 | 200 | 45 | 41.8 | 149 |
| ESCAT-140 | 200 | 15 | 12.4 | 48 |
| ESCAT-440 | 200 | 96 | 34.3 | 1.5 |
| ESCAT-440 | 150 | 75 | 42.2 | 6.5 |
| ESCAT-440 | 120 | 39 | 19 | n/d |
| ESCAT-340 | 220 | 50.2 | 50.2 | 70 |
| ESCAT-268 | 220 | 35.5 | 35.5 | n/d |
| Co-0138 E 1/16 3F | 200 | 58.6 | 32.0 | 18 |
| G 106 B/W 5% Rh | 220 | 95.8 | 90.8 | 142 |
| * ESCAT-340 | 200 | 40.4 | 38.0 | n/d |
| G 106 B/W 5% Rh | 220 | 93.6 | 89.4 | 134 |

2Py = 2-pyrrolidinone;

n/d = not detected;

* reaction was conducted at 2000 psig.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of processing an initial compound having a formula (A)

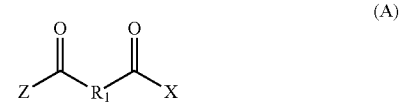

(A)

wherein $R_1$ comprises a saturated or unsaturated, branched or un-branched group containing from 1 to 10 carbon atoms, and wherein Z and X independently comprise one or more of C, H, O, N, S, a halide, and a counter-ion, the method comprising:

converting the initial compound to a cyclic compound having a formula (B)

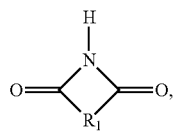

(B)

the converting comprising one or both of thermal and catalytic processing, the cyclic compound being present in a mixture comprising one or more additional components; and performing a purification to remove at least some of the one or more additional components.

2. The method of claim 1 wherein the converting and purification are conducted in a single reactor.

3. The method of claim 1 further comprising:

providing the purified form of compound (B) to a second reactor; and in the presence of a catalyst, hydrogenating the purified compound (B) to produce a pyrrolidinone compound having formula (C)

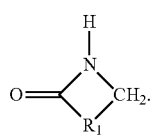

(C)

4. The method of claim 3 wherein the converting further comprises providing a first solution into a first reactor, the first solution comprising ammonia and the initial compound having formula (A), the first solution having a first ratio of ammonia to the initial compound.

5. The method of claim 4 wherein the converting further comprises:

adjusting the ratio of ammonia to produce a second solution having a second ratio of ammonia relative to the initial compound of from 1:1 to 1.5:1; and cyclizing the initial compound to form the compound having the formula (B).

6. The method of claim 4 wherein the initial compound comprises

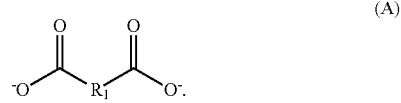

(A)

7. The method of claim 6 wherein $R_1$ is selected from the group consisting of branched and un-branched hydrocarbons having from 1 to 10 carbons.

8. The method of claim 1 wherein the performing the purification comprises at least one of decanting, distillation, sublimation, reactive distillation, steam distillation, extraction and crystallization.

9. The method of claim 1 wherein the converting is conducted at a temperature of from greater than about 100° C. to about 400° C.

10. The method of claim 1 wherein the converting is a catalytic process.

11. The method of claim 10 wherein the catalyst comprises one or more of Fe, Ni, Pd, Sn, Pt, Co, Re, Rh, Ir, Os, Ag, Au, Ru, Zr, and Cu.

* * * * *